United States Patent
Scheller et al.

(10) Patent No.: US 9,474,812 B2
(45) Date of Patent: Oct. 25, 2016

(54) INSTRUMENT STERILIZATION CONTAINER

(71) Applicant: Katalyst Surgical, LLC, Chesterfield, MO (US)

(72) Inventors: Gregg D Scheller, Wildwood, MO (US); Matthew N Zeid, Ballwin, MO (US); Matthew N Yates, High Ridge, MO (US)

(73) Assignee: Katalyst Surgical, LLC, Chesterfield, MO (US)

(*) Notice: Subject to any disclaimer, the term of this patent is extended or adjusted under 35 U.S.C. 154(b) by 0 days.

(21) Appl. No.: 14/631,910

(22) Filed: Feb. 26, 2015

(65) Prior Publication Data

US 2015/0273091 A1    Oct. 1, 2015

Related U.S. Application Data

(60) Provisional application No. 61/971,304, filed on Mar. 27, 2014.

(51) Int. Cl.
*A61L 2/04*    (2006.01)
*A61L 2/07*    (2006.01)

(52) U.S. Cl.
CPC .. *A61L 2/04* (2013.01); *A61L 2/07* (2013.01); *A61L 2202/122* (2013.01); *A61L 2202/24* (2013.01)

(58) Field of Classification Search
CPC .................................... A61L 2/04; A61L 2/07
See application file for complete search history.

(56) References Cited

U.S. PATENT DOCUMENTS

| | | | | |
|---|---|---|---|---|
| 4,135,868 A * | 1/1979 | Schainholz | ............... | A61L 2/26 206/438 |
| 4,541,992 A * | 9/1985 | Jerge | ...................... | A61C 19/02 422/300 |
| 4,798,292 A * | 1/1989 | Hauze | ...................... | A61L 2/26 206/210 |
| 4,959,199 A * | 9/1990 | Brewer | .................. | A61C 19/00 206/439 |
| 5,215,726 A * | 6/1993 | Kudla | ........................ | A61L 2/26 206/370 |
| 5,346,677 A * | 9/1994 | Risk | ........................ | A61C 19/02 206/363 |

(Continued)

OTHER PUBLICATIONS

Steve Charles, Techniques and tools for dissection of epiretinal membranes, Graefe' Arch Clin Exp Ophthalmol, 241:347-352, 2003.

*Primary Examiner* — Regina M Yoo
(74) *Attorney, Agent, or Firm* — Kevin P. Rollins

(57) ABSTRACT

An instrument sterilization container may include a base, a lid, a retention mechanism extending out from a base floor of the base, a first support mechanism extending out from a lid top of the lid, and a second support mechanism extending out from the base floor. A reusable instrument handle may be disposed between the first support mechanism, the second support mechanism, the retention mechanism, and a portion of the base. The portion of the base and the retention mechanism may be configured to prevent an actuation structure of the reusable instrument handle from extending during a sterilization of the reusable instrument handle in a medical autoclave. The first support mechanism and the second support mechanism may be configured to prevent the actuation structure from expanding during a sterilization of the reusable instrument handle in a medical autoclave.

20 Claims, 8 Drawing Sheets

(56) References Cited

U.S. PATENT DOCUMENTS

| | | | |
|---|---|---|---|
| 5,355,871 | A | 10/1994 | Hurley et al. |
| 5,370,658 | A | 12/1994 | Scheller et al. |
| 5,384,103 | A * | 1/1995 | Miller .................. A61C 19/02 16/438 |
| 5,433,929 | A * | 7/1995 | Riihimaki ................ A61L 2/26 206/263 |
| 5,759,502 | A * | 6/1998 | Spencer .................. A61L 2/26 206/370 |
| 5,843,387 | A * | 12/1998 | Dane ...................... A61L 2/26 206/363 |
| 5,893,873 | A | 4/1999 | Rader et al. |
| 5,913,422 | A * | 6/1999 | Cote ...................... A61L 2/26 206/210 |
| 5,921,998 | A | 7/1999 | Tano et al. |
| 6,488,695 | B1 | 12/2002 | Hickingbotham |
| 6,575,989 | B1 | 6/2003 | Scheller et al. |
| 6,730,076 | B2 | 5/2004 | Hickingbotham |
| 6,863,668 | B2 | 3/2005 | Gillespie et al. |
| 7,632,242 | B2 | 12/2009 | Griffin et al. |
| 7,766,904 | B2 | 8/2010 | McGowan, Sr. et al. |
| 8,038,692 | B2 | 10/2011 | Valencia et al. |
| 8,197,468 | B2 | 6/2012 | Scheller et al. |
| 2003/0171762 | A1 | 9/2003 | Forchette et al. |
| 2005/0154403 | A1 | 7/2005 | Sauer et al. |
| 2006/0235382 | A1 | 10/2006 | Cohen et al. |
| 2007/0104609 | A1 * | 5/2007 | Powell .................... A61L 2/26 422/1 |
| 2007/0185514 | A1 | 8/2007 | Kirchhevel |
| 2007/0282348 | A1 | 12/2007 | Lumpkin |
| 2008/0183199 | A1 | 7/2008 | Attinger |
| 2009/0228066 | A1 | 9/2009 | Hirata et al. |
| 2012/0116361 | A1 | 5/2012 | Hanlon et al. |
| 2013/0085326 | A1 | 4/2013 | Scheller et al. |
| 2013/0197488 | A1 | 8/2013 | Scheller et al. |
| 2014/0066977 | A1 | 3/2014 | Scheller et al. |
| 2014/0121697 | A1 | 5/2014 | Scheller et al. |
| 2014/0128909 | A1 | 5/2014 | Scheller et al. |
| 2014/0142603 | A1 | 5/2014 | Scheller et al. |
| 2014/0172010 | A1 | 6/2014 | Vezzu |
| 2014/0277110 | A1 | 9/2014 | Scheller et al. |
| 2015/0088193 | A1 | 3/2015 | Scheller et al. |

\* cited by examiner

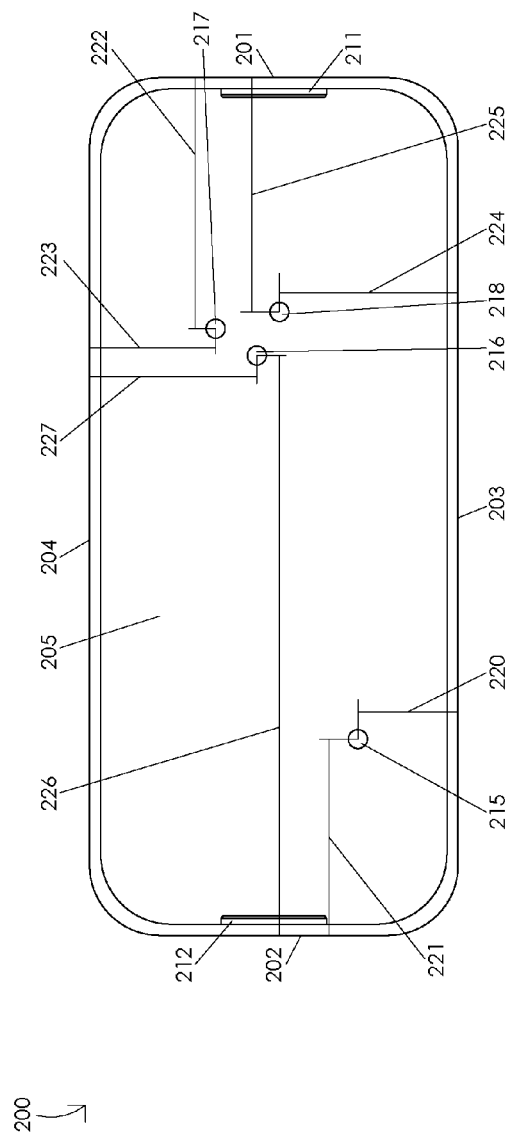
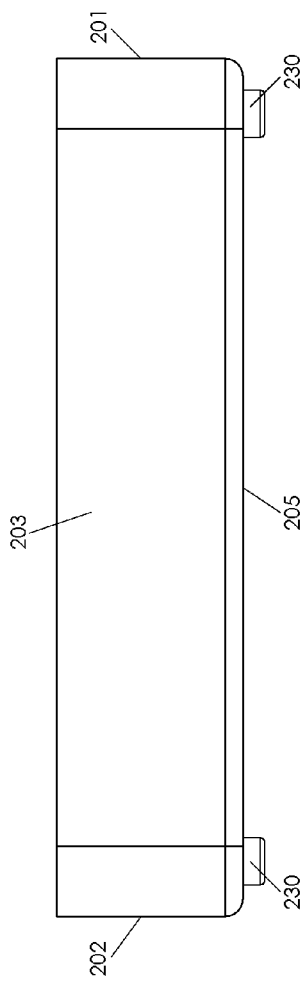

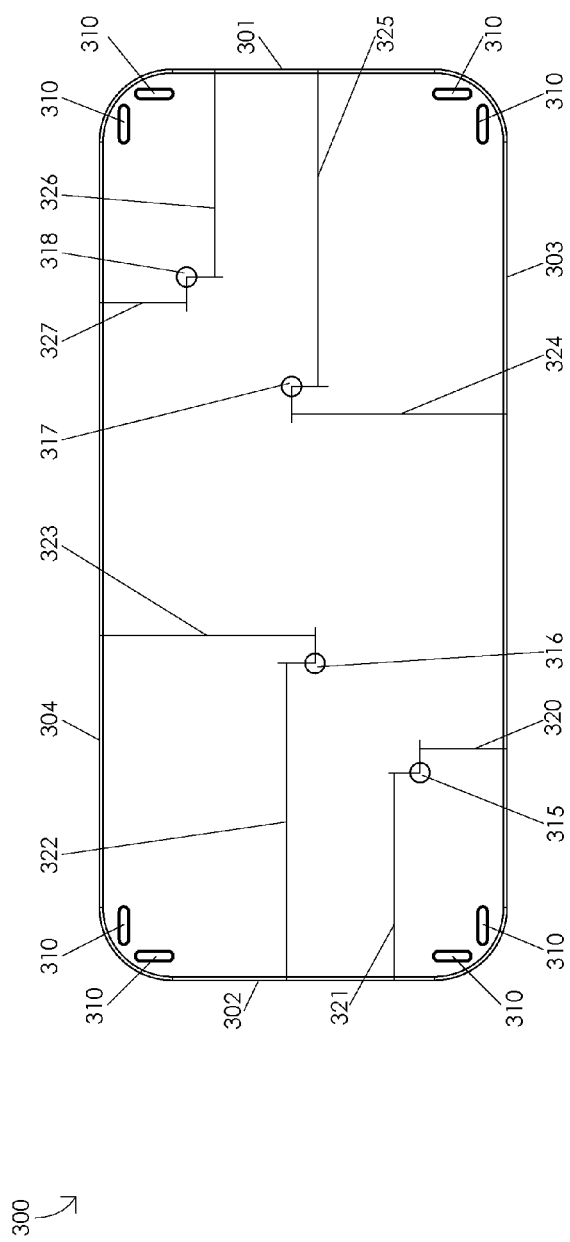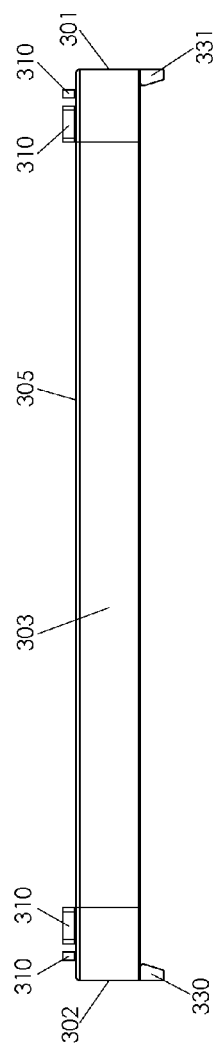
FIG. 3A
FIG. 3B

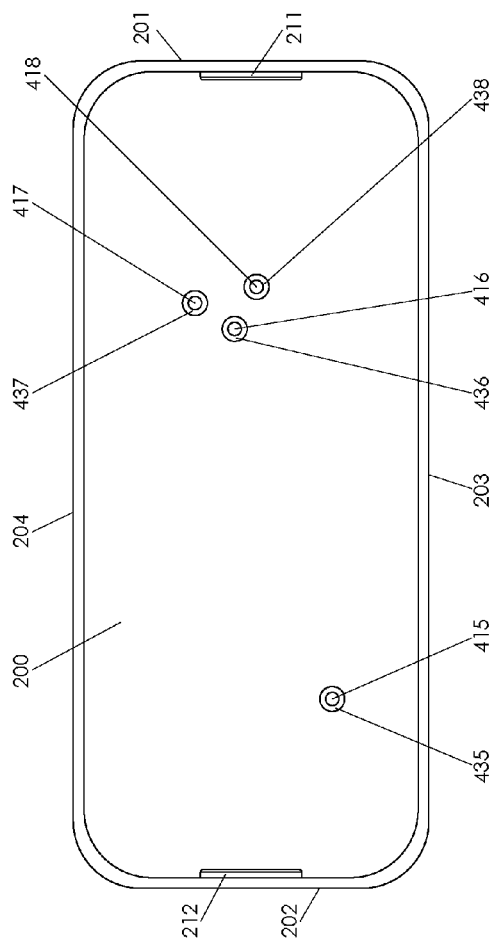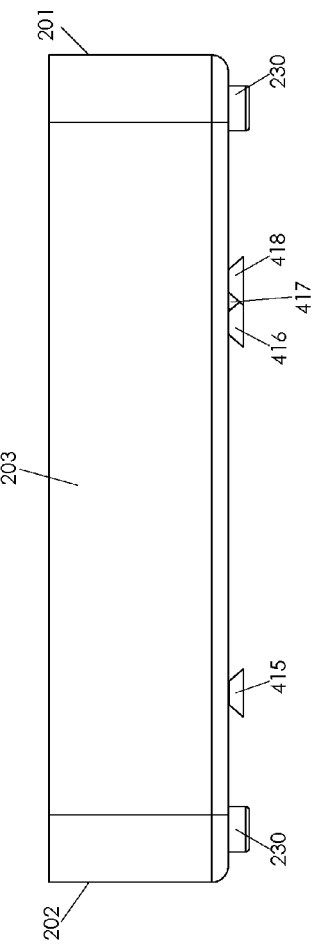
FIG. 5A
FIG. 5B

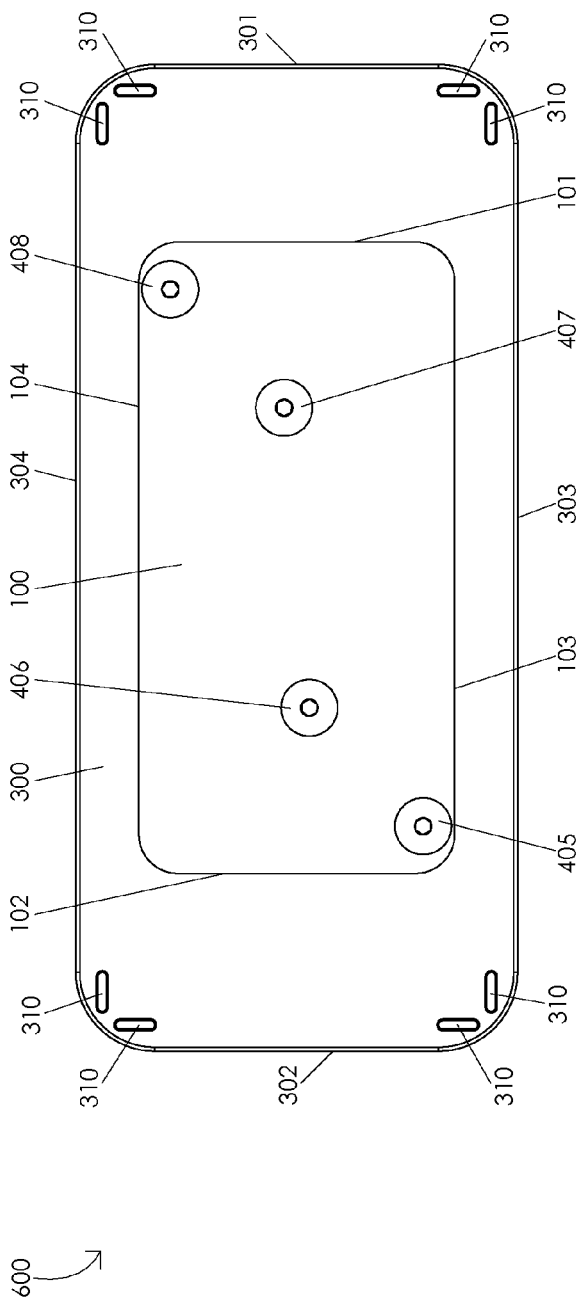
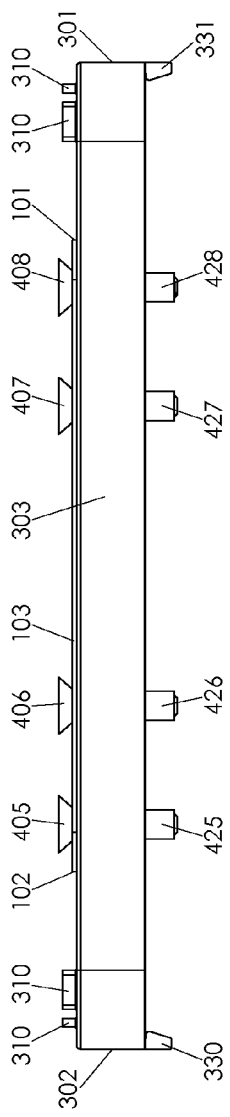
FIG. 6A
FIG. 6B

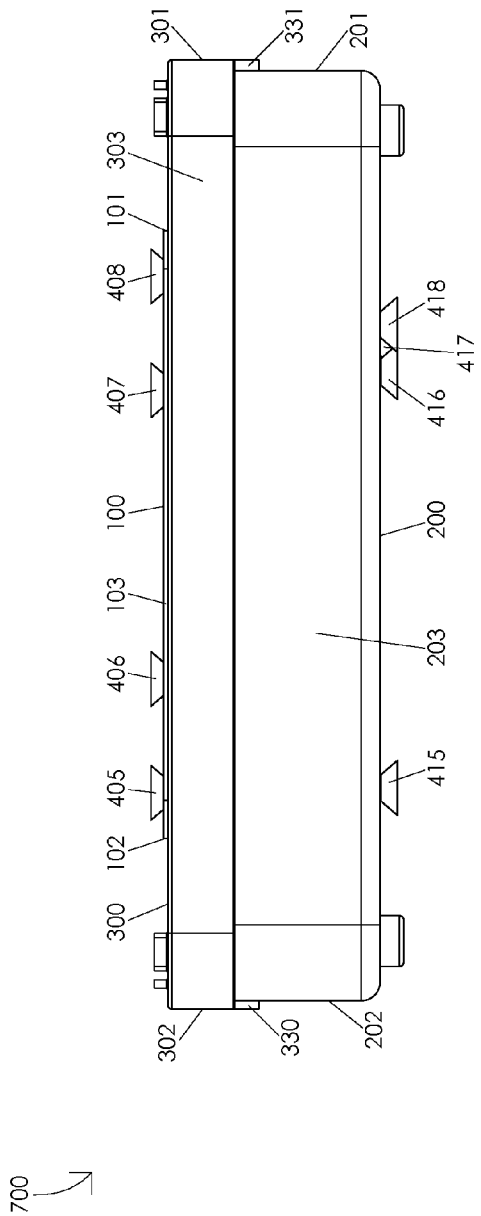
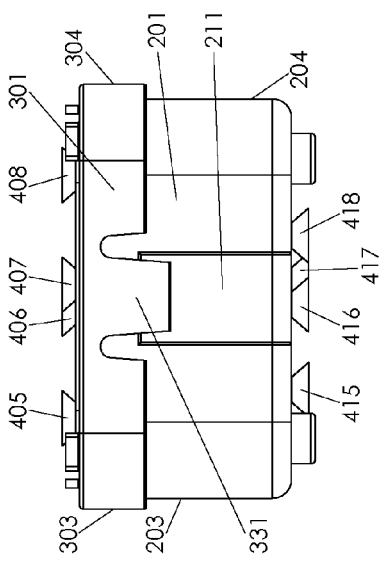
FIG. 7A
FIG. 7B

INSTRUMENT STERILIZATION CONTAINER

CROSS-REFERENCE TO RELATED APPLICATIONS

This Application claims the benefit of U.S. Provisional Application No. 61/971,304, filed Mar. 27, 2014.

FIELD OF THE INVENTION

The present disclosure relates to a medical device container, and, more particularly, to an instrument sterilization container.

BACKGROUND OF THE INVENTION

A wide variety of surgical instruments are reusable. Reusable surgical instruments must be cleaned and sterilized before use in surgery. Many reusable surgical instruments are steam sterilized within a medical autoclave after a surgeon completes a surgical procedure. Typically, reusable surgical instruments are collected, e.g., by a technician, after the instruments have been used in surgery. The used, non-sterile surgical instruments are then sterilized in a medical autoclave. Once sterilized, an instrument is ready for use in another surgical procedure.

Reusable microsurgical instruments, e.g., ophthalmic surgical instruments, are frequently damaged during cleaning and sterilization. These instruments are particularly susceptible to damage due to their micro-scale dimensions. Moreover, instrument components manufactured from polymers, e.g., thermoplastics, may experience undesirable changes after exposure to high temperature steam in a medical autoclave. For example, an actuation structure of an instrument handle may extend a first distance when compresses prior to sterilization in a medical autoclave. The actuation structure of the instrument handle may expand slightly during sterilization in a medical autoclave. After sterilization, the actuation structure of the instrument handle may extend a second distance when compressed and the instrument may no longer function as intended. Accordingly, there is a need for protecting reusable microsurgical instruments during sterilization in a medical autoclave and for ensuring reusable microsurgical instruments function as intended after sterilization in a medical autoclave.

BRIEF SUMMARY OF THE INVENTION

An instrument sterilization container is presented. In one or more embodiments, an instrument sterilization container may comprise a base, a lid, a retention mechanism extending out from a base floor of the base, a first support mechanism extending out from a lid top of the lid, and a second support mechanism extending out from the base floor. Illustratively, a reusable instrument handle may be disposed between the first support mechanism, the second support mechanism, the retention mechanism, and a portion of the base. In one or more embodiments, the portion of the base and the retention mechanism may be configured to prevent an actuation structure of the reusable instrument handle from extending during a sterilization of the reusable instrument handle in a medical autoclave. Illustratively, the first support mechanism and the second support mechanism may be configured to prevent the actuation structure from expanding during a sterilization of the reusable instrument handle in a medical autoclave.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A and 2B are schematic diagrams illustrating a base;

FIGS. 3A and 3B are schematic diagrams illustrating a lid;

FIGS. 5A and 5B are schematic diagrams illustrating an assembled base;

FIGS. 6A and 6B are schematic diagrams illustrating an assembled lid;

FIGS. 7A and 7B are schematic diagrams illustrating an assembled instrument sterilization container;

DETAILED DESCRIPTION OF AN ILLUSTRATIVE EMBODIMENT

Figure 1:
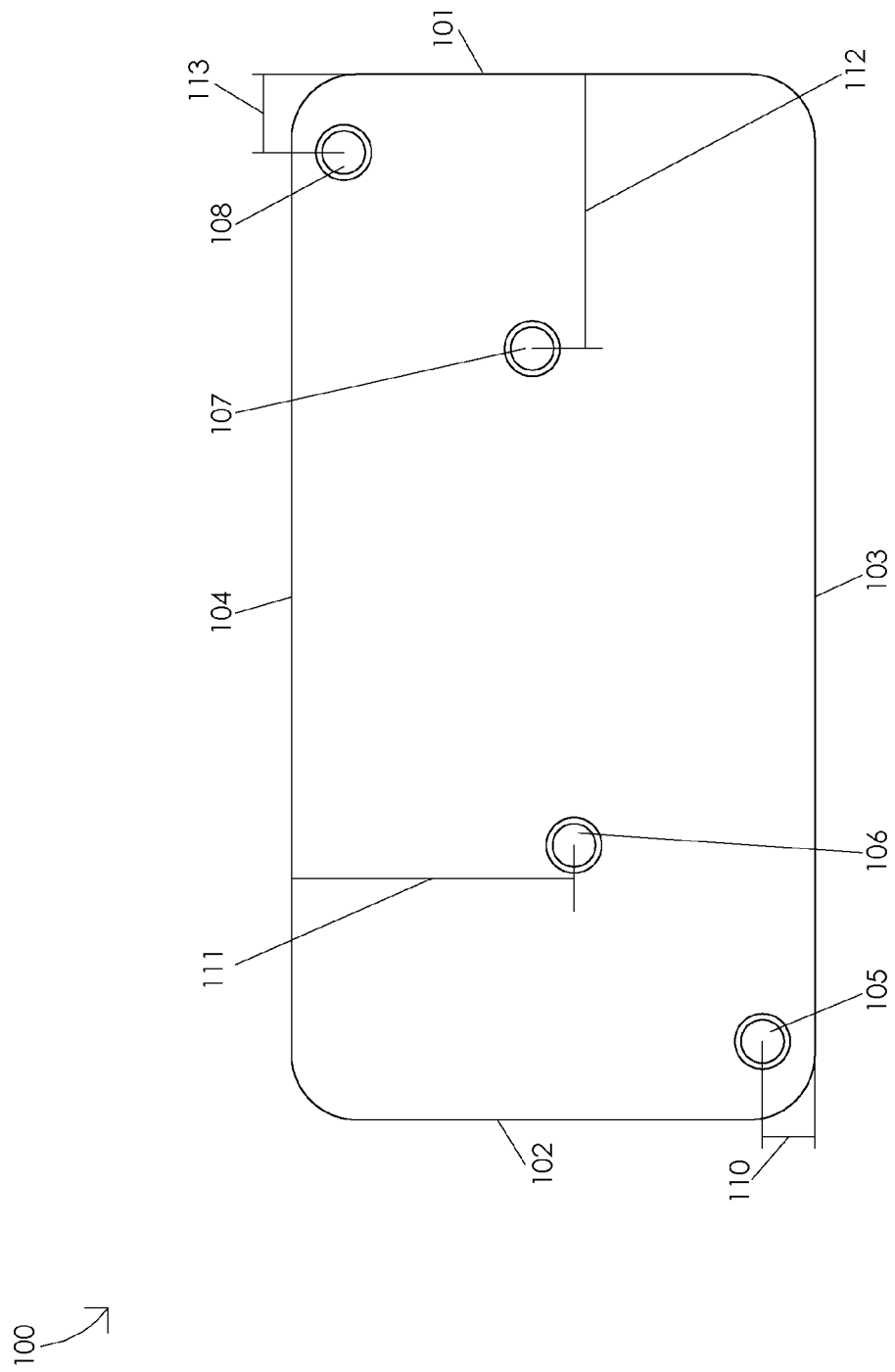
FIG. 1 is a schematic diagram illustrating a nameplate.

FIG. 1 is a schematic diagram illustrating a nameplate 100. Nameplate 100 may be configured to convey information, e.g., nameplate 100 may be configured to convey sterilization information. In one or more embodiments, nameplate 100 may comprise a nameplate distal end 101, a nameplate proximal end 102, a nameplate dorsal end 103, a nameplate ventral end 104, a first nameplate aperture 105, a second nameplate aperture 106, a third nameplate aperture 107, and a fourth nameplate aperture 108. Illustratively, first nameplate aperture 105 may be disposed a first nameplate distance 110 from nameplate dorsal end 103. In one or more embodiments, first nameplate distance 110 may be a distance in a range of 0.1 to 0.3 inches, e.g., first nameplate distance 110 may be a distance of 0.2 inches. Illustratively, first nameplate distance 110 may be a distance of less than 0.1 inches or greater than 0.3 inches. In one or more embodiments, second nameplate aperture 106 may be disposed a second nameplate distance 111 from nameplate ventral end 104. Illustratively, second nameplate distance 111 may be a distance in a range of 0.9 to 1.2 inches, e.g., second nameplate distance 111 may be a distance of 1.08 inches. In one or more embodiments, second nameplate distance 111 may be a distance of less than 0.9 inches or greater than 1.2 inches. Illustratively, third nameplate aperture 107 may be disposed a third nameplate distance 112 from nameplate distal end 101. In one or more embodiments, third nameplate distance 112 may be a distance in a range of 0.9 to 1.2 inches, e.g., third nameplate distance 112 may be a distance of 1.05 inches. Illustratively, third nameplate distance 112 may be a distance of less than 0.9 inches or greater than 1.2 inches. In one or more embodiments, fourth nameplate aperture 108 may be disposed a forth nameplate distance 113 from nameplate distal end 101. Illustratively, forth nameplate distance 113 may be a distance in a range of 0.2 to 0.4 inches, e.g., fourth nameplate distance 113 may be a distance of 0.3 inches. In one or more embodiments, fourth nameplate distance 113 may be a distance of less than 0.2 inches or greater than 0.4 inches.

Illustratively, nameplate 100 may be manufactured from any suitable material, e.g., polymers, metals, metal alloys, etc., or from any combination of suitable materials. In one or more embodiments, nameplate 100 may be manufactured from a material suitable for sterilization in a medical autoclave. Illustratively, nameplate 100 may be manufactured from a material configured to withstand exposure to temperatures, pressures, and ambient conditions present in a medical autoclave without degradation. For example, nameplate 100 may be configured to function normally after exposure in a temperature 250° F. for 15 minutes at an atmospheric pressure of 15 psi.

FIGS. 2A and 2B are schematic diagrams illustrating a base 200. FIG. 2A illustrates a top view of base 200. FIG. 2B illustrates a side view of base 200. In one or more embodiments, base 200 may comprise a base distal end 201, a base proximal end 202, a base dorsal end 203, a base ventral end 204, a base floor 205, a distal lip 211, a proximal lip 212, a third support mechanism housing 215, a fourth support mechanism housing 216, a first retention mechanism housing 217, a second retention mechanism housing 218, and a base hoist 230. Illustratively, base floor 205 may comprise one or more apertures configured to facilitate sterilization in a medical autoclave, e.g., base floor 205 may be configured to facilitate ingress of steam into base 200 and egress of steam out from base 200. In one or more embodiments, base hoist 230 may be configured to facilitate sterilization in a medical autoclave, e.g., base hoist 230 may be configured to facilitate ingress of steam into base 200 and egress of steam out from base 200.

Illustratively, third support mechanism housing 215 may be disposed a first base distance 220 from base dorsal end 203. In one or more embodiments, first base distance 220 may be a distance in a range of 0.6 to 0.8 inches, e.g., first base distance 220 may be a distance of 0.715 inches. Illustratively, first base distance 220 may be a distance of less than 0.6 inches or greater than 0.8 inches. In one or more embodiments, third support mechanism housing 215 may be disposed a second base distance 221 from base proximal end 202. Illustratively, second base distance 221 may be a distance in a range of 1.2 to 1.6 inches, e.g., second base distance 221 may be a distance of 1.403 inches. In one or more embodiments, second base distance 221 may be a distance of less than 1.2 inches or greater than 1.6 inches.

Illustratively, first retention mechanism housing 217 may be disposed a third base distance 222 from base distal end 201. In one or more embodiments, third base distance 222 may be a distance in a range of 1.6 to 1.9 inches, e.g., third base distance 222 may be a distance of 1.793 inches. Illustratively, third base distance 222 may be a distance of less than 1.6 inches or greater than 1.9 inches. In one or more embodiments, first retention mechanism housing 217 may be disposed a fourth base distance 223 from base ventral end 204. Illustratively, fourth base distance 223 may be a distance in a range of 0.8 to 1.0 inches, e.g., fourth base distance 223 may be a distance of 0.9 inches. In one or more embodiments, fourth base distance 223 may be a distance of less than 0.8 inches or greater than 1.0 inches.

Illustratively, second retention mechanism housing 218 may be disposed a fifth base distance 224 from base dorsal end 203. In one or more embodiments, fifth base distance 224 may be a distance in a range of 1.1 to 1.4 inches, e.g., fifth base distance 224 may be a distance of 1.275 inches. Illustratively, fifth base distance 224 may be a distance of less than 1.1 inches or greater than 1.4 inches. In one or more embodiments, second retention mechanism housing 218 may be disposed a sixth base distance 225 from base distal end 201. Illustratively, sixth base distance 225 may be a distance in a range of 1.4 to 1.8 inches, e.g., sixth base distance 225 may be a distance of 1.673 inches. In one or more embodiments, sixth base distance 225 may be a distance of less than 1.4 inches or greater than 1.8 inches.

Illustratively, fourth support mechanism housing 216 may be disposed a seventh base distance 226 from base proximal end 202. In one or more embodiments, seventh base distance 226 may be a distance in a range of 3.8 to 4.4 inches, e.g., seventh base distance 226 may be a distance of 4.141 inches. Illustratively, seventh base distance 226 may be a distance of less than 3.8 inches or greater than 4.4 inches. In one or more embodiments, fourth support mechanism housing 216 may be disposed an eighth base distance 227 from base ventral end 204. Illustratively, eighth base distance 227 may be a distance in a range of 0.8 to 1.4 inches, e.g., eighth base distance 227 may be a distance of 1.194 inches. In one or more embodiments, eighth base distance 227 may be a distance of less than 0.8 inches or greater than 1.4 inches.

Illustratively, base 200 may be manufactured from any suitable material, e.g., polymers, metals, metal alloys, etc., or from any combination of suitable materials. In one or more embodiments, base 200 may be manufactured from a material suitable for sterilization in a medical autoclave. Illustratively, base 200 may be manufactured from a material configured to withstand exposure to temperatures, pressures, and ambient conditions present in a medical autoclave without degradation. For example, base 200 may be configured to function normally after exposure in a temperature 250° F. for 15 minutes at an atmospheric pressure of 15 psi.

FIGS. 3A and 3B are schematic diagrams illustrating a lid 300. FIG. 3A illustrates a top view of lid 300. FIG. 3B illustrates a side view of lid 300. In one or more embodiments, lid 300 may comprise a lid distal end 301, a lid proximal end 302, a lid dorsal end 303, a lid ventral end 304, a lid top 305, a lid projection 310, a first support mechanism housing 315, a first alternative support mechanism housing 316, a second support mechanism housing 317, a second alternative support mechanism housing 318, a proximal barb 330, and a distal barb 331. Illustratively, proximal barb 330 may be configured to interface with proximal lip 212 and distal barb 331 may be configured to interface with distal lip 211 to temporarily attach lid 300 to base 200. For example, a portion of proximal barb 330 and a portion of distal barb 331 may be configured to temporarily attach lid 300 to base 200 by creating a friction force with a portion of proximal lip 212 and distal lip 211, respectively. Illustratively, lid top 305 may comprise one or more apertures configured to facilitate sterilization in a medical autoclave, e.g., lid top 305 may comprise one or more apertures configured to facilitate ingress of steam into base 200 and egress of steam out from base 200.

In one or more embodiments, first support mechanism housing 315 may be disposed a first lid distance 320 from lid dorsal end 303. Illustratively, first lid distance 320 may be a distance in a range of 0.4 to 0.8 inches, e.g., first lid distance 320 may be a distance of 0.598 inches. In one or more embodiments, first lid distance 320 may be a distance of less than 0.4 inches or greater than 0.8 inches. Illustratively, first support mechanism housing 315 may be disposed a second lid distance 321 from lid proximal end 320. In one or more embodiments, second lid distance 321 may be a distance in a range of 1.25 to 1.75 inches, e.g., second lid distance 321 may be a distance of 1.425 inches. Illustratively, second lid distance 321 may be a distance of less than 1.25 inches or greater than 1.75 inches.

In one or more embodiments, first alternative support mechanism housing 316 may be disposed a third lid distance 322 from lid proximal end 302. Illustratively, third lid distance 322 may be a distance in a range of 1.8 to 2.3 inches, e.g., third lid distance 322 may be a distance of 2.175 inches. In one or more embodiments, third lid distance 322 may be a distance of less than 1.8 inches or greater than 2.3 inches. Illustratively, first alternative support mechanism housing 316 may be disposed a fourth lid distance 323 from lid ventral end 304. In one or more embodiments, fourth lid distance 323 may be a distance in a range of 1.2 to 1.7 inches, e.g., forth lid distance 323 may be a distance of 1.478 inches. Illustratively, fourth lid distance 323 may be a distance of less than 1.2 inches or greater than 1.7 inches.

In one or more embodiments, second support mechanism housing 317 may be disposed a fifth lid distance 324 from lid dorsal end 303. Illustratively, fifth lid distance 324 may be a distance in a range of 1.2 to 1.7 inches, e.g., fifth lid distance 324 may be a distance of 1.478 inches. In one or more embodiments, fifth lid distance 324 may be a distance of less than 1.2 inches or greater than 1.7 inches. Illustratively, second support mechanism housing 317 may be disposed a sixth lid distance 325 from lid distal end 301. In one or more embodiments, sixth lid distance 325 may be a distance in a range of 1.8 to 2.4 inches, e.g., sixth lid distance 325 may be a distance of 2.175 inches. Illustratively, sixth lid distance 325 may be a distance of less than 1.8 inches or greater than 2.4 inches.

In one or more embodiments, second alternative support mechanism housing 318 may be disposed a seventh lid distance 327 from lid distal end 301. Illustratively, seventh lid distance 327 may be a distance in a range of 1.2 to 1.8 inches, e.g., seventh lid distance 327 may be a distance of 1.425 inches. In one or more embodiments, seventh lid distance 327 may be a distance of less than 1.2 inches or greater than 1.8 inches. Illustratively, second alternative support mechanism housing 318 may be disposed an eighth lid distance 327 from lid ventral end 304. In one or more embodiments, eighth lid distance 327 may be a distance in a range of 0.4 to 0.8 inches, e.g., eighth lid distance 327 may be a distance of 0.598 inches. Illustratively, eighth lid distance 327 may be a distance of less than 0.4 inches or greater than 0.8 inches.

Illustratively, lid 300 may be manufactured from any suitable material, e.g., polymers, metals, metal alloys, etc., or from any combination of suitable materials. In one or more embodiments, lid 300 may be manufactured from a material suitable for sterilization in a medical autoclave. Illustratively, lid 300 may be manufactured from a material configured to withstand exposure to temperatures, pressures, and ambient conditions present in a medical autoclave without degradation. For example, lid 300 may be configured to function normally after exposure in a temperature 250° F. for 15 minutes at an atmospheric pressure of 15 psi.

Figure 4:
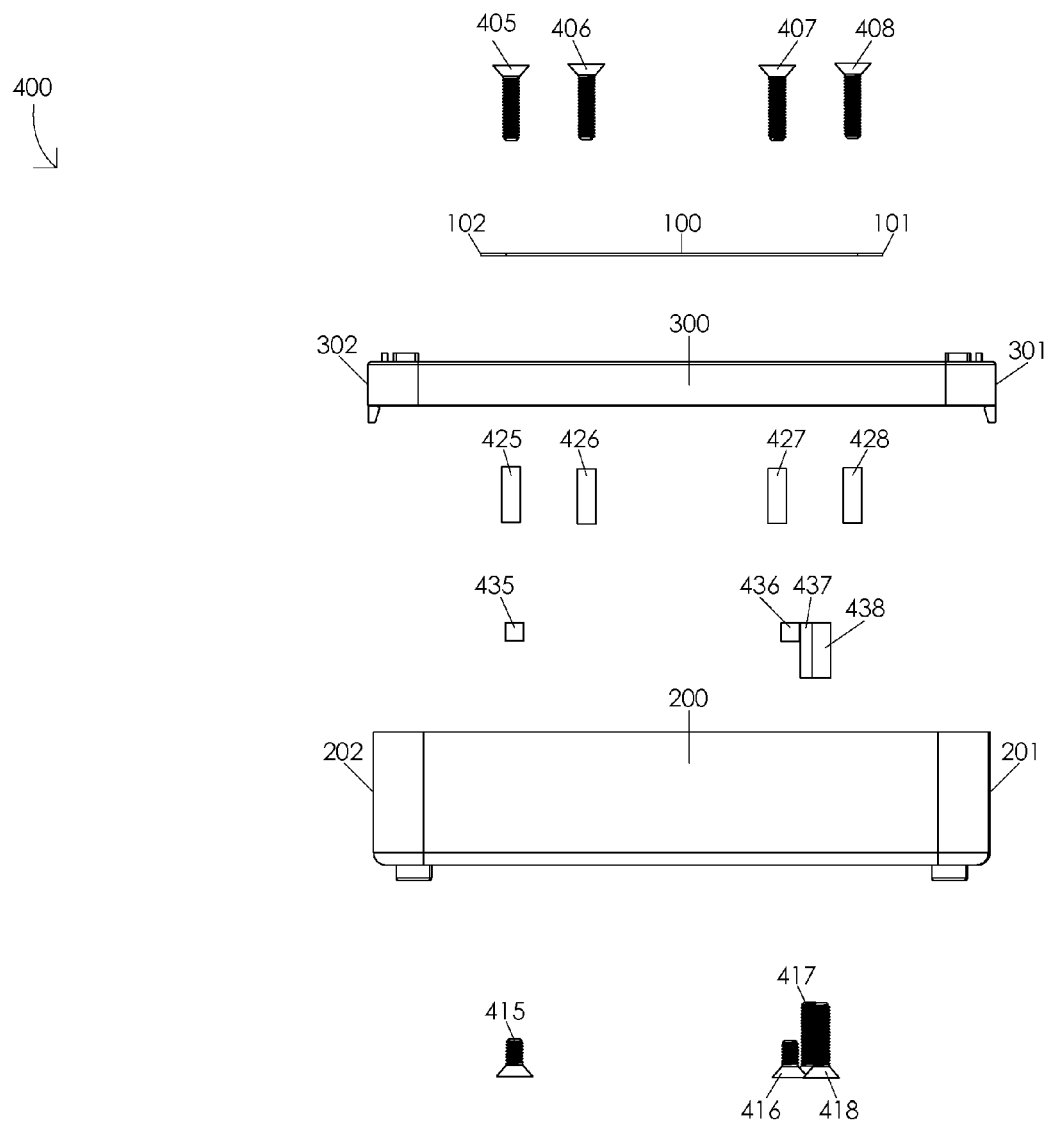
FIG. 4 is a schematic diagram illustrating an exploded view of an instrument sterilization container assembly.

FIG. 4 is a schematic diagram illustrating an exploded view of an instrument sterilization container assembly 400. In one or more embodiments, instrument sterilization container assembly 400 may comprise a nameplate 100, a base 200, a lid 300, a first support mechanism 405, a first alternative support mechanism 406, a second support mechanism 407, a second alternative support mechanism 408, a third support mechanism 415, a fourth support mechanism 416, a first retention mechanism 417, a second retention mechanism 418, a first support mechanism sleeve 425, a first alternative support mechanism sleeve 426, a second support mechanism sleeve 427, a second alternative support mechanism sleeve 428, a third support mechanism sleeve 435, a fourth support mechanism sleeve 436, a first retention mechanism sleeve 437, and a second retention mechanism sleeve 438.

FIGS. 5A and 5B are schematic diagrams illustrating an assembled base 500. FIG. 5A illustrates a top view of assembled base 500. FIG. 5B illustrates a side view of assembled base 500. In one or more embodiments, third support mechanism 415 may be disposed within third support mechanism housing 215. Illustratively, third support mechanism 415 may be threaded and third support mechanism housing 215 may have threading corresponding to threading of third support mechanism 415. In one or more embodiments, third support mechanism 415 may be fixed within third support mechanism housing 215. For example, third support mechanism 415 may be fixed within third support mechanism housing 215 by an adhesive, an interference fit, a weld, or any suitable fixation means. Illustratively, third support mechanism 415 may be disposed within third support mechanism housing 215 wherein a portion of third support mechanism 415 extends out from base floor 205 and into base 200. In one or more embodiments, third support mechanism 415 may be disposed within third support mechanism housing 215 wherein a portion of third support mechanism 415 extends out from base floor 205 a distance in a range of 0.5 to 0.6 inches, e.g., a portion of third support mechanism 415 may extend out from base floor 205 a distance of 0.55 inches. Illustratively, third support mechanism 415 may be disposed within third support mechanism housing 215 wherein a portion of third support mechanism 415 extends out from base floor 205 a distance of less than 0.5 inches or greater than 0.6 inches.

In one or more embodiments, third support mechanism sleeve 435 may be manufactured from any suitable material, e.g., polymers, metals, metal alloys, etc., or from any combination of suitable materials. Illustratively, third support mechanism sleeve 435 may comprise a silicon tube, e.g., third support mechanism sleeve 435 may comprise a heat stabilized silicon tube configured for use at temperatures up to 500° F. In one or more embodiments, third support mechanism sleeve 435 may comprise a material having a hardness rating in a range of 55 to 70 Shore A, e.g., third support mechanism sleeve 435 may comprise a material having a hardness rating of 60 Shore A. Illustratively, third support mechanism sleeve 435 may have an outer diameter in a range of 0.17 to 0.2 inches, e.g., third support mechanism sleeve 435 may have an outer diameter of 0.185 inches. In one or more embodiments, third support mechanism sleeve 435 may have an outer diameter of less than 0.17 inches or greater than 0.2 inches. Illustratively, third support mechanism sleeve 435 may have an inner diameter in a range of 0.09 inches to 0.11 inches, e.g., third support mechanism sleeve 435 may have an inner diameter of 0.104 inches. In one or more embodiments, third support mechanism sleeve 435 may be disposed over a portion of third support mechanism 415, e.g., third support mechanism sleeve 435 may be disposed over a portion of third support mechanism 415 extending out from base floor 205 and into base 200. Illustratively, third support mechanism sleeve 435 may be fixed to a portion of third support mechanism 415 by an adhesive, an interference fit, a weld, or any suitable fixation means.

In one or more embodiments, fourth support mechanism 416 may be disposed within fourth support mechanism housing 216. Illustratively, fourth support mechanism 416 may be threaded and fourth support mechanism housing 216 may have threading corresponding to threading of fourth support mechanism 416. In one or more embodiments, fourth support mechanism 416 may be fixed within fourth support mechanism housing 216. For example, fourth support mechanism 416 may be fixed within fourth support mechanism housing 216 by an adhesive, an interference fit, a weld, or any suitable fixation means. Illustratively, fourth support mechanism 416 may be disposed within fourth support mechanism housing 216 wherein a portion of fourth support mechanism 416 extends out from base floor 205 and into base 200. In one or more embodiments, fourth support mechanism 416 may be disposed within fourth support mechanism housing 216 wherein a portion of fourth support mechanism 416 extends out from base floor 205 a distance in a range of 0.5 to 0.6 inches, e.g., a portion of fourth support mechanism 416 may extend out from base floor 205 a distance of 0.55 inches. Illustratively, fourth support port mechanism 416 may be disposed within fourth support mechanism housing 216 wherein a portion of fourth support mechanism 416 extends out from base floor 205 a distance of less than 0.5 inches or greater than 0.6 inches.

In one or more embodiments, fourth support mechanism sleeve 436 may be manufactured from any suitable material, e.g., polymers, metals, metal alloys, etc., or from any combination of suitable materials. Illustratively, fourth support mechanism sleeve 436 may comprise a silicon tube, e.g., fourth support mechanism sleeve 436 may comprise a heat stabilized silicon tube configured for use at temperatures up to 500° F. In one or more embodiments, fourth support mechanism sleeve 436 may comprise a material having a hardness rating in a range of 55 to 70 Shore A, e.g., fourth support mechanism sleeve 436 may comprise a material having a hardness rating of 60 Shore A. Illustratively, fourth support mechanism sleeve 436 may have an outer diameter in a range of 0.17 to 0.2 inches, e.g., fourth support mechanism sleeve 436 may have an outer diameter of 0.185 inches. In one or more embodiments, fourth support mechanism sleeve 436 may have an outer diameter of less than 0.17 inches or greater than 0.2 inches. Illustratively, fourth support mechanism sleeve 436 may have an inner diameter in a range of 0.09 inches to 0.11 inches, e.g., fourth support mechanism sleeve 436 may have an inner diameter of 0.104 inches. In one or more embodiments, fourth support mechanism sleeve 436 may be disposed over a portion of fourth support mechanism 416, e.g., fourth support mechanism sleeve 436 may be disposed over a portion of fourth support mechanism 416 extending out from base floor 205 and into base 200. Illustratively, fourth support mechanism sleeve 436 may be fixed to a portion of fourth support mechanism 416 by an adhesive, an interference fit, a weld, or any suitable fixation means.

In one or more embodiments, first retention mechanism 417 may be disposed within first retention mechanism housing 217. Illustratively, first retention mechanism 417 may be threaded and first retention mechanism housing 217 may have threading corresponding to threading of first retention mechanism 417. In one or more embodiments, first retention mechanism 417 may be fixed within first retention mechanism housing 217. For example, first retention mechanism 417 may be fixed within first retention mechanism housing 217 by an adhesive, an interference fit, a weld, or any suitable fixation means. Illustratively, first retention mechanism 417 may be disposed within first retention mechanism housing 217 wherein a portion of first retention mechanism 417 extends out from base floor 205 and into base 200. In one or more embodiments, first retention mechanism 417 may be disposed within first retention mechanism housing 217 wherein a portion of first retention mechanism 417 extends out from base floor 205 a distance in a range of 0.3 to 0.7 inches, e.g., a portion of first retention mechanism 417 may extend out from base floor 205 a distance of 0.55 inches. Illustratively, first retention mechanism 417 may be disposed within first retention mechanism housing 217 wherein a portion of first retention mechanism 417 extends out from base floor 205 a distance of less than 0.3 inches or greater than 0.7 inches.

In one or more embodiments, first retention mechanism sleeve 437 may be manufactured from any suitable material, e.g., polymers, metals, metal alloys, etc., or from any combination of suitable materials. Illustratively, first retention mechanism sleeve 437 may comprise a silicon tube, e.g., first retention mechanism sleeve 437 may comprise a heat stabilized silicon tube configured for use at temperatures up to 500° F. In one or more embodiments, first retention mechanism sleeve 437 may comprise a material having a hardness rating in a range of 55 to 70 Shore A, e.g., first retention mechanism sleeve 437 may comprise a material having a hardness rating of 60 Shore A. Illustratively, first retention mechanism sleeve 437 may have an outer diameter in a range of 0.17 to 0.2 inches, e.g., first retention mechanism sleeve 437 may have an outer diameter of 0.185 inches. In one or more embodiments, first retention mechanism sleeve 437 may have an outer diameter of less than 0.17 inches or greater than 0.2 inches. Illustratively, first retention mechanism sleeve 437 may have an inner diameter in a range of 0.09 inches to 0.11 inches, e.g., first retention mechanism sleeve 437 may have an inner diameter of 0.104 inches. In one or more embodiments, first retention mechanism sleeve 437 may be disposed over a portion of first retention mechanism 417, e.g., first retention mechanism sleeve 437 may be disposed over a portion of first retention mechanism 417 extending out from base floor 205 and into base 200. Illustratively, first retention mechanism sleeve 437 may be fixed to a portion of first retention mechanism 417 by an adhesive, an interference fit, a weld, or any suitable fixation means.

In one or more embodiments, second retention mechanism 418 may be disposed within second retention mechanism housing 218. Illustratively, second retention mechanism 418 may be threaded and second retention mechanism housing 218 may have threading corresponding to threading of second retention mechanism 418. In one or more embodiments, second retention mechanism 418 may be fixed within second retention mechanism housing 218. For example, second retention mechanism 418 may be fixed within second retention mechanism housing 218 by an adhesive, an interference fit, a weld, or any suitable fixation means. Illustratively, second retention mechanism 418 may be disposed within second retention mechanism housing 218 wherein a portion of second retention mechanism 418 extends out from base floor 205 and into base 200. In one or more embodiments, second retention mechanism 418 may be disposed within second retention mechanism housing 218 wherein a portion of second retention mechanism 418 extends out from base floor 205 a distance in a range of 0.3 to 0.7 inches, e.g., a portion of second retention mechanism 418 may extend out from base floor 205 a distance of 0.55 inches. Illustratively, second retention mechanism 418 may be disposed within second retention mechanism housing 218 wherein a portion of second retention mechanism 418 extends out from base floor 205 a distance of less than 0.3 inches or greater than 0.7 inches.

In one or more embodiments, second retention mechanism sleeve 438 may be manufactured from any suitable material, e.g., polymers, metals, metal alloys, etc., or from any combination of suitable materials. Illustratively, second retention mechanism sleeve 438 may comprise a silicon tube, e.g., second retention mechanism sleeve 438 may comprise a heat stabilized silicon tube configured for use at temperatures up to 500° F. In one or more embodiments, second retention mechanism sleeve 438 may comprise a material having a hardness rating in a range of 55 to 70 Shore A, e.g., second retention mechanism sleeve 438 may comprise a material having a hardness rating of 60 Shore A. Illustratively, second retention mechanism sleeve 438 may have an outer diameter in a range of 0.17 to 0.2 inches, e.g., second retention mechanism sleeve 438 may have an outer diameter of 0.185 inches. In one or more embodiments, second retention mechanism sleeve 438 may have an outer diameter of less than 0.17 inches or greater than 0.2 inches. Illustratively, second retention mechanism sleeve 438 may have an inner diameter in a range of 0.09 inches to 0.11 inches, e.g., second retention mechanism sleeve 438 may have an inner diameter of 0.104 inches. In one or more embodiments, second retention mechanism sleeve 438 may be disposed over a portion of second retention mechanism 418, e.g., second retention mechanism sleeve 438 may be disposed over a portion of second retention mechanism 418 extending out from base floor 205 and into base 200. Illustratively, second retention mechanism sleeve 438 may be fixed to a portion of second retention mechanism 418 by an adhesive, an interference fit, a weld, or any suitable fixation means.

FIGS. 6A and 6B are schematic diagrams illustrating an assembled lid 600. FIG. 6A illustrates a top view of assembled lid 600. FIG. 6B illustrates a side view of assembled lid 600. In one or more embodiments, first support mechanism 405 may be configured to attach nameplate 100 to lid 300, e.g., first support mechanism 405 may be disposed within nameplate 100 and lid 300. Illustratively, first support mechanism 405 may be disposed within first nameplate aperture 105 and first support mechanism housing 315. In one or more embodiments, first support mechanism 405 may be threaded and first support mechanism housing 315 may have threading corresponding to threading of first support mechanism 405. Illustratively, first support mechanism 405 may be fixed within first support mechanism housing 315. In one or more embodiments, a fixation of first support mechanism 405 within first support mechanism housing 315 may be configured to attach nameplate 100 to lid top 305. Illustratively, first support mechanism 405 may be fixed within first support mechanism housing 315 by an adhesive, an interference fit, a weld, or any suitable fixation means. In one or more embodiments, first support mechanism 405 may be disposed within first nameplate aperture 105 and first support mechanism housing 315 wherein a portion of first support mechanism 405 extends out from lid top 305. Illustratively, first support mechanism 405 may be disposed within first nameplate aperture 105 and first support mechanism housing 315 wherein a portion of first support mechanism 405 extends out from lid top 305 a distance in a range of 0.5 to 0.6 inches, e.g., a portion of first support mechanism 405 may extend out from lid top 305 a distance of 0.55 inches. In one or more embodiments, first support mechanism 405 may be disposed within first nameplate aperture 105 and first support mechanism housing 315 wherein a portion of first support mechanism 405 extends out from lid top 305 a distance of less than 0.5 inches or greater than 0.6 inches.

In one or more embodiments, first support mechanism sleeve 425 may be manufactured from any suitable material, e.g., polymers, metals, metal alloys, etc., or from any combination of suitable materials. Illustratively, first support mechanism sleeve 425 may comprise a silicon tube, e.g., first support mechanism sleeve 425 may comprise a heat stabilized silicon tube configured for use at temperatures up to 500° F. In one or more embodiments, first support mechanism sleeve 425 may comprise a material having a hardness rating in a range of 55 to 70 Shore A, e.g., first support mechanism sleeve 425 may comprise a material having a hardness rating of 60 Shore A. Illustratively, first support mechanism sleeve 425 may have an outer diameter in a range of 0.17 to 0.2 inches, e.g., first support mechanism sleeve 425 may have an outer diameter of 0.185 inches. In one or more embodiments, first support mechanism sleeve 425 may have an outer diameter of less than 0.17 inches or greater than 0.2 inches. Illustratively, first support mechanism sleeve 425 may have an inner diameter in a range of 0.09 inches to 0.11 inches, e.g., first support mechanism sleeve 425 may have an inner diameter of 0.104 inches. In one or more embodiments, first support mechanism sleeve 425 may be disposed over a portion of first support mechanism 405, e.g., first support mechanism sleeve 425 may be disposed over a portion of first support mechanism 405 extending out from lid top 305. Illustratively, first support mechanism sleeve 425 may be fixed to a portion of first support mechanism 405 by an adhesive, an interference fit, a weld, or any suitable fixation means.

In one or more embodiments, first alternative support mechanism 406 may be configured to attach nameplate 100 to lid 300, e.g., first alternative support mechanism 406 may be disposed within nameplate 100 and lid 300. Illustratively, first alternative support mechanism 406 may be disposed within second nameplate aperture 106 and first alternative support mechanism housing 316. In one or more embodiments, first alternative support mechanism 406 may be threaded and first alternative support mechanism housing 316 may have threading corresponding to threading of first alternative support mechanism 406. Illustratively, first alternative support mechanism 406 may be fixed within first alternative support mechanism housing 316. In one or more embodiments, a fixation of first alternative support mechanism 406 within first alternative support mechanism housing 316 may be configured to attach nameplate 100 to lid top 305. Illustratively, first alternative support mechanism 406 may be fixed within first alternative support mechanism housing 316 by an adhesive, an interference fit, a weld, or any suitable fixation means. In one or more embodiments, first alternative support mechanism 406 may be disposed within second nameplate aperture 106 and first alternative support mechanism housing 316 wherein a portion of first alternative support mechanism 406 extends out from lid top 305. Illustratively, first alternative support mechanism 406 may be disposed within second nameplate aperture 106 and first alternative support mechanism housing 316 wherein a portion of first alternative support mechanism 406 extends out from lid top 305 a distance in a range of 0.5 to 0.6 inches, e.g., a portion of first alternative support mechanism 406 may extend out from lid top 305 a distance of 0.55 inches. In one or more embodiments, first alternative support mechanism 406 may be disposed within second nameplate aperture 106 and first alternative support mechanism housing 316 wherein a portion of first alternative support mechanism 406 extends out from lid top 305 a distance of less than 0.5 inches or greater than 0.6 inches.

In one or more embodiments, first alternative support mechanism sleeve 426 may be manufactured from any suitable material, e.g., polymers, metals, metal alloys, etc., or from any combination of suitable materials. Illustratively, first alternative support mechanisms sleeve 426 may comprise a silicon tube, e.g., first alternative support mechanism sleeve 426 may comprise a heat stabilized silicon tube configured for use at temperatures up to 500° F. In one or more embodiments, first alternative support mechanism sleeve 426 may comprise a material having a hardness rating in a range of 55 to 70 Shore A, e.g., first alternative support mechanism sleeve 426 may comprise a material having a hardness rating of 60 Shore A. Illustratively, first alternative support mechanism sleeve 426 may have an outer diameter in a range of 0.17 to 0.2 inches, e.g., first alternative support mechanism sleeve 426 may have an outer diameter of 0.185 inches. In one or more embodiments, first alternative support mechanism sleeve 426 may have an outer diameter of less than 0.17 inches or greater than 0.2 inches. Illustratively, first alternative support mechanism sleeve 426 may have an inner diameter in a range of 0.09 inches to 0.11 inches, e.g., first alternative support mechanism sleeve 426 may have an inner diameter of 0.104 inches. In one or more embodiments, first alternative support mechanism sleeve 426 may be disposed over a portion of first alternative support mechanism 406, e.g., first alternative support mechanism sleeve 426 may be disposed over a portion of first alternative support mechanism 406 extending out from lid top 305. Illustratively, first alternative support mechanism sleeve 426 may be fixed to a portion of first alternative support mechanism 406 by an adhesive, an interference fit, a weld, or any suitable fixation means.

In one or more embodiments, second support mechanism 407 may be configured to attach nameplate 100 to lid 300, e.g., second support mechanism 407 may be disposed within nameplate 100 and lid 300. Illustratively, second support mechanism 407 may be disposed within third nameplate aperture 107 and second support mechanism housing 317. In one or more embodiments, second support mechanism 407 may be threaded and second support mechanism housing 317 may have threading corresponding to threading of second support mechanism 407. Illustratively, second support mechanism 407 may be fixed within second support mechanism housing 317. In one or more embodiments, a fixation of second support mechanism 407 within second support mechanism housing 317 may be configured to attach nameplate 100 to lid top 305. Illustratively, second support mechanism 407 may be fixed within second support mechanism housing 317 by an adhesive, an interference fit, a weld, or any suitable fixation means. In one or more embodiments, second support mechanism 407 may be disposed within third nameplate aperture 107 and second support mechanism housing 317 wherein a portion of second support mechanism 407 extends out from lid top 305. Illustratively, second support mechanism 407 may be disposed within third nameplate aperture 107 and second support mechanism housing 317 wherein a portion of second support mechanism 407 extends out from lid top 305 a distance in a range of 0.5 to 0.6 inches, e.g., a portion of second support mechanism 407 may extend out from lid top 305 a distance of 0.55 inches. In one or more embodiments, second support mechanism 407 may be disposed within third nameplate aperture 107 and second support mechanism housing 317 wherein a portion of second support mechanism 407 extends out from lid top 305 a distance of less than 0.5 inches or greater than 0.6 inches.

In one or more embodiments, second support mechanism sleeve 427 may be manufactured from any suitable material, e.g., polymers, metals, metal alloys, etc., or from any combination of suitable materials. Illustratively, second support mechanism sleeve 427 may comprise a silicon tube, e.g., second support mechanism sleeve 427 may comprise a heat stabilized silicon tube configured for use at temperatures up to 500° F. In one or more embodiments, second support mechanism sleeve 427 may comprise a material having a hardness rating in a range of 55 to 70 Shore A, e.g., second support mechanism sleeve 427 may comprise a material having a hardness rating of 60 Shore A. Illustratively, second support mechanism sleeve 427 may have an outer diameter in a range of 0.17 to 0.2 inches, e.g., second support mechanism sleeve 427 may have an outer diameter of 0.185 inches. In one or more embodiments, second support mechanism sleeve 427 may have an outer diameter of less than 0.17 inches or greater than 0.2 inches. Illustratively, second support mechanism sleeve 427 may have an inner diameter in a range of 0.09 inches to 0.11 inches, e.g., second support mechanism sleeve 427 may have an inner diameter of 0.104 inches. In one or more embodiments, second support mechanism sleeve 427 may be disposed over a portion of second support mechanism 407, e.g., second support mechanism sleeve 427 may be disposed over a portion of second support mechanism 407 extending out from lid top 305. Illustratively, second support mechanism sleeve 427 may be fixed to a portion of second support mechanism 407 by an adhesive, an interference fit, a weld, or any suitable fixation means.

In one or more embodiments, second alternative support mechanism 408 may be configured to attach nameplate 100 to lid 300, e.g., second alternative support mechanism 408 may be disposed within nameplate 100 and lid 300. Illustratively, second alternative support mechanism 408 may be disposed within fourth nameplate aperture 108 and second alternative support mechanism housing 318. In one or more embodiments, second alternative support mechanism 408 may be threaded and second alternative support mechanism housing 318 may have threading corresponding to threading of second alternative support mechanism 408. Illustratively, second alternative support mechanism 408 may be fixed within second alternative support mechanism housing 318. In one or more embodiments, a fixation of second alternative support mechanism 408 within second alternative support mechanism housing 318 may be configured to attach nameplate 100 to lid top 305. Illustratively, second alternative support mechanism 408 may be fixed within second alternative support mechanism housing 318 by an adhesive, an interference fit, a weld, or any suitable fixation means. In one or more embodiments, second alternative support mechanism 408 may be disposed within fourth nameplate aperture 108 and second alternative support mechanism housing 318 wherein a portion of second alternative support mechanism 408 extends out from lid top 305. Illustratively, second alternative support mechanism 408 may be disposed within fourth nameplate aperture 108 and second alternative support mechanism housing 318 wherein a portion of second alternative support mechanism 408 extends out from lid top 305 a distance in a range of 0.5 to 0.6 inches, e.g., a portion of second alternative support mechanism 408 may extend out from lid top 305 a distance of 0.55 inches. In one or more embodiments, second alternative support mechanism 408 may be disposed within fourth nameplate aperture 108 and second alternative support mechanism housing 318 wherein a portion of second alternative support mechanism 408 extends out from lid top 305 a distance of less than 0.5 inches or greater than 0.6 inches.

In one or more embodiments, second alternative support mechanism sleeve 428 may be manufactured from any suitable material, e.g., polymers, metals, metal alloys, etc., or from any combination of suitable materials. Illustratively, second alternative support mechanism sleeve 428 may comprise a silicon tube, e.g., second alternative support mechanism sleeve 428 may comprise a heat stabilized silicon tube configured for use at temperatures up to 500° F. In one or more embodiments, second alternative support mechanism sleeve 428 may comprise a material having a hardness rating in a range of 55 to 70 Shore A, e.g., second alternative support mechanism sleeve 428 may comprise a material having a hardness rating of 60 Shore A. Illustratively, second alternative support mechanism sleeve 428 may have an outer diameter in a range of 0.17 to 0.2 inches, e.g., second alternative support mechanism sleeve 428 may have an outer diameter of 0.185 inches. In one or more embodiments, second alternative support mechanism sleeve 428 may have an outer diameter of less than 0.17 inches or greater than 0.2 inches. Illustratively, second alternative support mechanism sleeve 428 may have an inner diameter in a range of 0.09 inches to 0.11 inches, e.g., second alternative support mechanism sleeve 428 may have an inner diameter of 0.104 inches. In one or more embodiments, second alternative support mechanism sleeve 428 may be disposed over a portion of second alternative support mechanism 408, e.g., second alternative support mechanism sleeve 428 may be disposed over a portion of second alternative support mechanism 408 extending out from lid top 305. Illustratively, second alternative support mechanism sleeve 428 may be fixed to a portion of second alternative support mechanism 408 by an adhesive, an interference fit, a weld, or any suitable fixation means.

FIGS. 7A and 7B are schematic diagrams illustrating an assembled instrument sterilization container 700. FIG. 7A illustrates a side view of assembled instrument sterilization container 700. FIG. 7B illustrates a front view of assembled instrument sterilization container 700. In one or more embodiments, assembled instrument sterilization container 700 may comprise assembled lid 600 attached to assembled base 500. Illustratively, proximal barb 330 may be configured to interface with proximal lip 212 and distal barb 331 may be configured to interface with distal lip 211 to temporarily attach lid 300 to base 200. In one or more embodiments, first support mechanism 405, first alternative support mechanism 406, second support mechanism 407, and second alternative support mechanism 408 may extend out from lid top 305 and into base 200 when assembled lid 600 is attached to assembled base 500.

Illustratively, a reusable surgical instrument, e.g., an ophthalmic surgical instrument, may be disposed within assembled instrument sterilization container 700 and assembled instrument sterilization container 700 may be disposed within a medical autoclave for sterilization of the reusable surgical instrument. In one or more embodiments, assembled instrument sterilization container 700 may be configured to prevent damage to a reusable surgical instrument, e.g., an ophthalmic surgical instrument, during sterilization in a medical autoclave. Illustratively, assembled sterilization container 700 may be configured to prevent expansion of reusable surgical instrument components, e.g., ophthalmic surgical instrument components, during sterilization in a medical autoclave. In one or more embodiments, assembled instrument sterilization container 700 may be configured to prevent deformation of reusable surgical instrument components, e.g., ophthalmic surgical instrument components, during sterilization in a medical autoclave.

Figure 8:
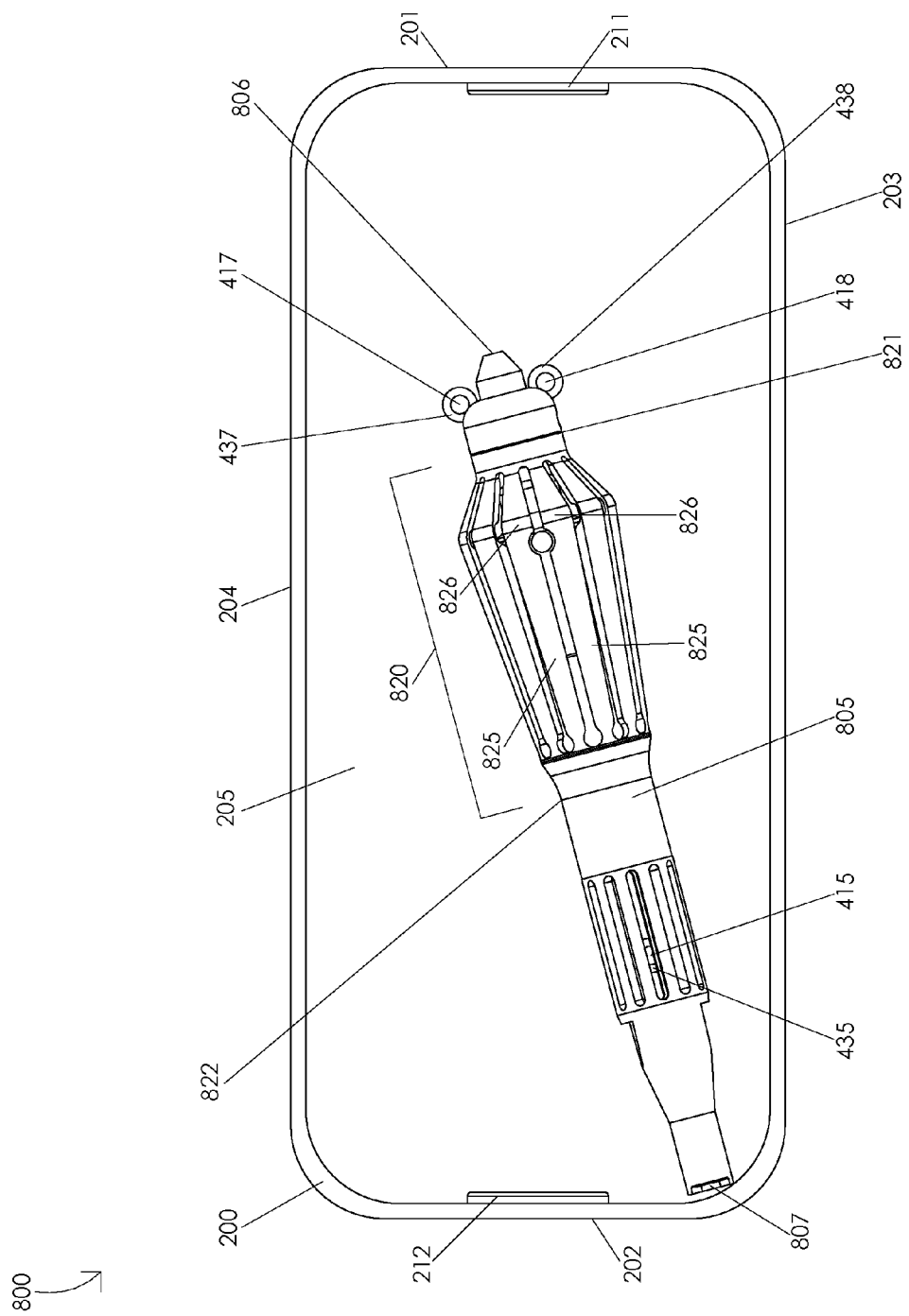
FIG. 8 is a schematic diagram illustrating an instrument orientation.

FIG. 8 is a schematic diagram illustrating an instrument orientation 800. In one or more embodiments, an instrument orientation 800 may comprise an instrument handle 805 having an instrument handle distal end 806 and an instrument handle proximal end 807. Illustratively, instrument handle 805 may comprise an actuation structure 820 having an actuation structure distal end 821 and an actuation structure proximal end 822. In one or more embodiments, actuation structure 820 may comprise a plurality of actuation arms 825 wherein each actuation arm 825 of the plurality of actuation arms 825 comprises an extension mechanism 826. Illustratively, actuation structure 820 may be configured to extend when compressed, e.g., a compression of actuation structure 820 may be configured to increase a distance between actuation structure distal end 821 and actuation structure proximal end 822. In one or more embodiments, actuation structure 820 may be configured to retract when decompressed, e.g., a decompression of actuation structure 820 may be configured to decrease a distance between actuation structure distal end 821 and actuation structure proximal end 822. Illustratively, actuation structure 820 may be manufactured from any suitable material, e.g., polymers, metals, metal alloys, etc., or from any combination of suitable materials. In one or more embodiments, actuation structure 820 may be manufactured from a synthetic polymer material, e.g., actuation structure 820 may be manufactured from a thermoplastic material. Illustratively, actuation structure 820 may be manufactured from a material configured to absorb water when sterilized in a medical autoclave, e.g., actuation structure 820 may be manufactured from a Nylon material.

Illustratively, instrument handle 805 may be disposed within assembled base 500 wherein a portion of instrument handle 805 is disposed over third support mechanism 415 and fourth support mechanism 416. In one or more embodiments, instrument handle 805 may be disposed within assembled base 500 wherein a portion of instrument handle 805 is disposed between first retention mechanism 417 and second retention mechanism 418. Illustratively, instrument handle 805 may be disposed within assembled base 500 and assembled lid 600 may be attached to assembled base 500 wherein first support mechanism 405 is disposed over a portion of instrument handle 805 and second support mechanism 407 is disposed over a portion of instrument handle 805. In one or more embodiments, instrument handle 805 may be disposed within assembled base 500 and assembled lid 600 may be attached to assembled base 500 wherein first alternative support mechanism 406 is disposed over a portion of instrument handle 805 and second alternative support mechanism 408 is disposed over a portion of instrument handle 805. Illustratively, assembled lid 600 may be configured to dispose first support mechanism 405 and second support mechanism 407 over a portion of instrument handle 805 when assembled lid 600 is in a first orientation. In one or more embodiments, assembled lid 600 may be configured to dispose first alternative support mechanism 406 and second alternative support mechanism 408 over a portion of instrument handle 805 when assembled lid 600 is in a second orientation. Illustratively, the second orientation may be the first orientation rotated 180 degrees about a center of assembled lid 600, e.g., the first orientation of assembled lid 600 may be a mirror image of the second orientation of assembled lid 600.

In one or more embodiments, instrument handle 805 may be disposed within assembled instrument sterilization container 700 wherein a portion of instrument handle 805 is disposed below first support mechanism 405 and second support mechanism 407, a portion of instrument handle 805 is disposed above third support mechanism 415 and fourth support mechanism 416, and a portion of instrument handle 805 is disposed between first retention mechanism 417 and second retention mechanism 418. Illustratively, instrument handle 805 may be disposed within assembled instrument sterilization container 700 wherein a portion of instrument handle 805 is disposed below first alternative support mechanism 406 and second alternative support mechanism 408, a portion of instrument handle 805 is disposed above third support mechanism 415 and fourth support mechanism 416, and a portion of instrument handle 805 is disposed between first retention mechanism 417 and second retention mechanism 418. In one or more embodiments, instrument handle 805 may be disposed within assembled instrument sterilization container 700 wherein a first portion of instrument handle 805 abuts first retention mechanism 417 and second retention mechanism 418 and a second portion of instrument handle 805 abuts a portion of base 200, e.g., instrument handle 805 may be disposed within assembled instrument sterilization container 700 wherein first retention mechanism 417, second retention mechanism 418, and a portion of base 200 prevent an extension of instrument handle distal end 806 relative to instrument handle proximal end 807 during a sterilization of instrument handle 805 in a medical autoclave. Illustratively, instrument handle 805 may be disposed within assembled instrument sterilization container 700 wherein first retention mechanism 417, second retention mechanism 418, and a portion of base 200 are configured to prevent an extension of instrument handle distal end 806 relative to handle proximal end 807 during a sterilization of instrument handle 805 in a medical autoclave, e.g., instrument handle 805 may be disposed within assembled instrument sterilization container 700 wherein first retention mechanism 417, second retention mechanism 418, and a portion of handle base 200 are configured to prevent an extension of actuation structure distal end 821 relative to actuation structure proximal end 822 during a sterilization of instrument handle 805 in a medical autoclave. In one or more embodiments, first retention mechanism sleeve 437 and second retention mechanism sleeve 438 may be configured to prevent damage to instrument handle 805 during a sterilization of instrument handle 805 in a medical autoclave, e.g., first retention mechanism sleeve 437 and second retention mechanism sleeve 438 may be configured to prevent damage to actuation structure 820 during a sterilization of instrument handle 805 in a medical autoclave.

In one or more embodiments, instrument handle 805 may be disposed within assembled instrument sterilization container 700 wherein first support mechanism 405, second support mechanism 407, third support mechanism 415, and fourth support mechanism 416 are configured to prevent an expansion of actuation structure 820 during a sterilization of instrument handle 805 in a medical autoclave. Illustratively, instrument handle 805 may be disposed within assembled instrument sterilization container 700 wherein first alternative support mechanism 406, second alternative support mechanism 408, third support mechanism 415, and fourth support mechanism 416 are configured to prevent an expansion of actuation structure 820 during a sterilization of instrument handle 805 in a medical autoclave. In one or more embodiments, instrument handle 805 may be disposed within assembled instrument sterilization container 700 wherein first support mechanism 405, second support mechanism 407, third support mechanism 415, and fourth support mechanism 416 are configured to prevent an expansion of each actuation arm 825 of the plurality of actuation arms 825 during a sterilization of instrument handle 805 in a medical autoclave. Illustratively, instrument handle 805 may be disposed within assembled instrument sterilization container 700 wherein first alternative support mechanism 406, second alternative support mechanism 408, third support mechanism 415, and fourth support mechanism 416 are configured to prevent an expansion of each actuation arm 825 of the plurality of actuation arms 826 during a sterilization of instrument handle 805 in a medical autoclave.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a sterilization container, the teachings of the present invention are equally suitable to any systems where the functionality may be employed. Therefore, it is the object of the appended claims to cover all such variations and modifications as come within the true spirit and scope of the invention.

What is claimed is:

1. A container comprising:
    a base having a base distal end, a base proximal end, a base dorsal end, and a base ventral end;
    a base floor of the base;
    a lid having a lid distal end, a lid proximal end, a lid dorsal end, and a lid ventral end;
    a lid top of the lid;
    a first support mechanism disposed in the lid, the first support mechanism extending a distance from the lid top;
    a second support mechanism disposed in the base, the second support mechanism extending a first distance from the base floor;
    a first retention mechanism disposed in the base, the first retention mechanism extending a second distance from the base floor wherein the first retention mechanism and a portion of the base are configured to prevent an extension of an actuation structure of a surgical instrument handle during a sterilization of the surgical instrument handle in a medical autoclave;
    a second retention mechanism disposed in the base, the second retention mechanism extending the second distance from the base floor wherein the second retention mechanism and the portion of the base are configured to prevent the extension of the actuation structure of the surgical instrument handle during the sterilization of the surgical instrument handle in the medical autoclave;
    a first retention mechanism sleeve disposed over a portion of the first retention mechanism; and
    a second retention mechanism sleeve disposed over a portion of the second retention mechanism.

2. The container of claim 1 further comprising:
    a third support mechanism disposed in the lid, the third support mechanism extending the distance from the lid top wherein the first support mechanism and the third support mechanism are configured to prevent an expansion of the actuation structure of the surgical instrument handle during the sterilization of the surgical instrument handle in the medical autoclave.

3. The container of claim 2 wherein the distance from the lid top is in a range of 0.5 to 0.6 inches.

4. The container of claim 1 wherein the second distance from the base floor is in a range of 0.3 to 0.7 inches.

5. The container of claim 1 further comprising:
    a distal lip of the base;
    a proximal lip of the base;
    a distal barb of the lid; and
    a proximal barb of the lid.

6. The container of claim 5 further comprising:
one or more apertures of the lid configured to facilitate an ingress of steam into the base during the sterilization of the surgical instrument handle in the medical autoclave.

7. The container of claim 6 further comprising:
one or more apertures of the base floor configured to facilitate the ingress of steam into the base during the sterilization of the surgical instrument handle in the medical autoclave.

8. The container of claim 1 wherein the first retention mechanism is disposed a distance in a range of 1.6 to 1.9 inches from the base distal end.

9. The container of claim 8 wherein the first retention mechanism is disposed a distance in a range of 0.8 to 1.0 inches from the base ventral end.

10. The container of claim 1 wherein the first support mechanism is disposed a distance in a range of 1.8 to 2.4 inches from the lid distal end.

11. The container of claim 10 where the first support mechanism is disposed a distance in a range of 1.2 to 1.7 inches from the lid dorsal end.

12. A container comprising:
a base having a base distal end, a base proximal end, a base dorsal end, and a base ventral end;
a base floor of the base;
a lid having a lid distal end, a lid proximal end, a lid dorsal end, and a lid ventral end;
a lid top of the lid;
a first support mechanism disposed in the lid, the first support mechanism extending out from the lid top;
a second support mechanism disposed in the lid, the second support mechanism extending out from the lid top;
a third support mechanism disposed in the base, the third support mechanism extending out from the base floor;
a first retention mechanism disposed in the base, the first retention mechanism extending out from the base floor;
a second retention mechanism disposed in the base, the second retention mechanism extending out from the base floor wherein the first retention mechanism and the second retention mechanism are configured to prevent an extension of an actuation structure of a surgical instrument handle during a sterilization of the surgical instrument handle in a medical autoclave; and
a first retention mechanism sleeve disposed over a portion of the first retention mechanism, the first retention mechanism sleeve configured to prevent damage to the actuation structure of the surgical instrument handle during the sterilization of the surgical instrument handle in the medical autoclave.

13. The container of claim 12 further comprising:
a fourth support mechanism disposed in the base, the fourth support mechanism extending out from the base floor.

14. The container of claim 12 wherein the first retention mechanism sleeve is manufactured from a material having a hardness rating in a range of 55 to 70 Shore A.

15. The container of claim 12 further comprising:
a first alternative support mechanism disposed in the lid, the first alternative support mechanism extending out from the lid top; and
a second alternative support mechanism disposed in the lid, the second alternative support mechanism extending out from the lid top.

16. The container of claim 12 further comprising:
a distal lip of the base; and
a proximal lip of the base.

17. The container of claim 12 further comprising:
a distal barb of the lid; and
a proximal barb of the lid.

18. The container of claim 12 further comprising:
one or more apertures of the lid configured to facilitate an ingress of steam into the base during the sterilization of the surgical instrument handle in the medical autoclave.

19. The container of claim 12 further comprising:
one or more apertures of the base floor configured to facilitate the ingress of steam into the base during the sterilization of the surgical instrument handle in the medical autoclave.

20. The container of claim 12 further comprising:
a plurality of actuation arms of the actuation structure.

* * * * *